United States Patent [19]

Quadbeck-Seeger et al.

[11] 4,032,568
[45] June 28, 1977

[54] PRODUCTION OF 2-HYDROXYNAPHTHALENE-3-CARBOXYLIC ACID

[75] Inventors: Hans-Juergen Quadbeck-Seeger; Helmut Hoch, both of Ludwigshafen, Germany

[73] Assignee: BASF Aktiengesellschaft, Ludwigshafen (Rhine), Germany

[22] Filed: Sept. 24, 1975

[21] Appl. No.: 616,446

Related U.S. Application Data

[63] Continuation of Ser. No. 476,151, June 3, 1974, abandoned.

[30] Foreign Application Priority Data

June 23, 1973  Germany .......................... 2332064

[52] U.S. Cl. .......................................... 260/520 A
[51] Int. Cl.$^2$ ......................................... C07C 51/15
[58] Field of Search ................................ 260/520 A

[56] References Cited

UNITED STATES PATENTS

| | | | |
|---|---|---|---|
| 1,725,394 | 8/1929 | Dreteile | 260/520 A |
| 2,132,356 | 10/1938 | Lecher et al. | 260/521 C |
| 2,807,643 | 9/1957 | Hartley | 260/521 C |
| 2,824,892 | 2/1958 | Barkley | 260/520 A |
| 3,405,169 | 10/1968 | Levy et al. | 260/520 A |
| 3,655,744 | 4/1972 | Yasuhara et al. | 260/520 A |

FOREIGN PATENTS OR APPLICATIONS

| | | | |
|---|---|---|---|
| 717,095 | 8/1965 | Canada | 260/520 A |
| 2,260,637 | 6/1974 | Germany | 260/520 A |

*Primary Examiner*—Norman Morgenstern
*Attorney, Agent, or Firm*—Keil, Thompson & Shurtleff

[57] ABSTRACT

2-hydroxynaphthalene-3-carboxylic acid is produced by heating a mixture of potassium β-naphtholate and sodium β-naphtholate to a temperature of at least 180° C, reacting it with carbon dioxide and treating the salt formed with an acid. The product is a dye intermediate, a coupling component of surface coating dyes and chrome dyes, and a developer for diazo dyes.

4 Claims, No Drawings

PRODUCTION OF 2-HYDROXYNAPHTHALENE-3-CARBOXYLIC ACID

This is a continuation of application Ser. No. 476,151 filed June 3, 1974, now abandoned.

The invention relates to a process for the production of 2-hydroxynaphthalene-3-carboxylic acid by heating a mixture of potassium β-naphtholate and sodium β-naphtholate to a temperature of at least 180° C, reacting it with carbon dioxide and treating the salt formed with an acid.

The well-known method of producing 2-hydroxynaphthalene-3-carboxylic acid from β-naphthol consists in converting β-naphthol by reaction with caustic soda solution into a sodium salt and then reacting the sodium salt with carbon dioxide at elevated temperature and superatmospheric pressure to form the disodium salt of 2-hydroxynaphthalene-3-carboxylic acid (BIOS Report No. 986, pages 234 et seq.; Ullmanns Encyklopadie de technischen Chemie, Volume 12, pages 606 et seq.). This method is unsatisfactory because it requires special apparatus and involves high operating and energy costs. A major difficulty of the method consists in the rapid and complete dehydration of the sodium β-naphtholate prior to the carboxylation reaction. The yield of disodium salt of 2-hydroxynaphthalene-3-carboxylic acid declines in the presence of even small amounts of water. Drying the sodium β-naphtholate is difficult and protracted. Since transfer of heat is unfavorable in the sodium β-naphtholate present as a solid, even carefully controlled heating and mixing of the naphtholate, which is a time-consuming and therefore costly operation, may not prevent local overheating, so that decomposition of the solid salt may occur.

Modifications have been developed to improve the said method: U.S. Pat. No. 2,132,357 discloses reaction of the sodium naphtholate in the presence of pyridine and its homologs. Nickel has to be used as the material of construction because iron vessels corrode and the iron compounds thus formed promote the formation of naphthoxanthone as a byproduct to a considerable extent. It is stated in the said patent specification that the good solubility of carbon dioxide in the solvent used is an important condition for rapid carboxylation. Odor nuisance and toxicity of the solvent are disadvantages of this method, especially in commercial operation. When the naphtholate is heated a large proportion of the solvent is distilled off in an azeotropic mixture with water and is lost to the reaction. Recovery of the solvent is difficult and expensive; fractions of the same remaining in the waste water provide environmental problems.

U.S. Pat. No. 2,132,356 discloses the use of cyclic ethers such as dioxane as a solvent for the reaction. As in the case of pyridine it is not possible to use iron as the material of construction. The ethers used are also largely removed from the reaction with the water so that the difficulties in processing referred to above also apply. A high reaction pressure has to be used. Safety problems also arise because dioxane and its derivatives may contain peroxide as a byproduct.

Paraffin wax and paraffin oil are disclosed as the reaction medium in U.S. Pat. No. 1,503,984; these substances retard the reaction and are difficult to recover. The process is troublesome and uneconomic, especially in commercial operation.

Dialkyketones are used in the process disclosed in British Pat. No. 638,196. Large amounts of solvent have to be used to achieve solution and this means heavy expenditure on materials and a low space-time yield.

German Laid-Open Specification (DOS) No. 2,132,296 discloses the use of diphenyl, diphenyl oxide or an alkylnaphthalene having an alkyl group of one to four carbon atoms as the reaction medium. The solvents are volatile in steam and the same difficulties are therefore met with in processing, recovery of the solvent and waste water disposal as described above. As compared with other solvents, alkylnapthalenes are more difficulty accessible and uneconomical compounds.

As taught in German Pat. No. 436,524, carboxylation of potassium β-naphtholate at above 170° C, for example at 170° to 230° C, gives mainly 2-hydroxynaphthalene-6-carboxylic acid and not the 3-carboxylic acid compound.

The object of the present invention is to provide a novel process for producing 2-hydroxynaphthalene-3-carboxylic acid in a good yield and purity and in a better space-time yield by a simpler and more economical method.

We have found that 2-hydroxynaphthalene-3-carboxylic acid is obtained advantageously in the reaction of sodium β-naphtholate with carbon monoxide at elevated temperature by heating, instead of sodium β-naphtholate, a mixture of sodium β-naphtholate and potassium β-naphtholate in a first stage to a temperature of at least 180° C, reacting it with carbon dioxide at the said temperature in a second stage and converting the salt of 2-hydroxynaphthalene-3-carboxylic acid thus formed into 2-hydroxynaphthalene-3-carboxylic acid by adding an acid.

We have further found that the reaction is carried out with advantage in the presence of araliphatic compounds containing at least two aromatic radicals joined together by means of a cycloaliphatic and/or aliphatic radical.

Moreover we have found that it is advantageous to carry out the reaction in the presence of an aromatic ether in which at least one aromatic radical is combined with at least one aliphatic, cycloaliphatic and/or araliphatic radical by way of an oxygen atom.

The reaction may be represented by the following equations:

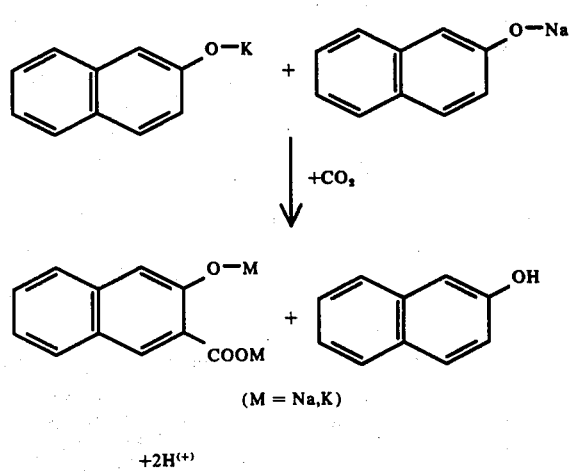

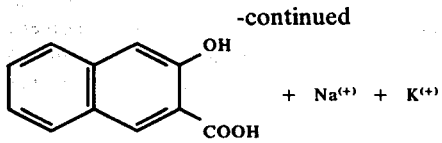

+ Na⁽⁺⁾ + K⁽⁺⁾

The process of the invention gives 2-hydroxynaphthalene-3-carboxylic acid in a good yield and purity and in better space-time yields in a simpler and more economical manner than the prior art methods. Dehydration takes place much more easily and rapidly upon heating the naphtholates. The dehydration period of the prior art methods can be shortened to one-tenth. Prior art methods which do not use any solvent moreover give at the end of the first stage a hard reaction mixture difficult to disintegrate which on an industrial scale has to be comminuted and ground with special equipment such as crushers or mills prior to the carboxylation stage; in the process of the invention viscous or mobile melts are generally obtained depending on the temperature and these may be supplied direct to the carboxylation. Accordingly costs of energy and materials are reduced and operating time and personnel are saved as compared with the prior art. Transfer of heat in the reaction mixture in the first stage of the process of the invention is more favorable and there is therefore no appreciable local overheating of the solid salt and hardly any decomposition which might decrease the yield. Moreover it is easier to treat a mobile liquid with a gas than to treat a solid. In the prior art methods the α-naphthol formed increases the agglutination and agglomeration of the reaction mixture. In contrast to this β-naphthol can easily be removed from the melts of the invention by distillation or stripping with a recycled stream of carbon dioxide.

The araliphatic compounds used according to the present invention in an advantageous embodiment are usually obtainable as byproducts of other syntheses, for example the polymerization or oligomerization of styrene and its derivatives or are readily accessible by Friedel-Crafts syntheses with benzyl chlorides and naphthalenemethyl chlorides and benzene, benzene derivatives or diphenylmethane and its homologs; for example the dibenzylbenzols and their mixtures of isomers prepared by the methods described in German Pat. No. 1,085,877 are suitable. The aromatic ethers used in another advantageous embodiment in accordance with the invention are readily accessible for example by reaction of an alkali metal phenolate with an alkyl or aralkyl halide or the corresponding sulfates. As compared with the use of cyclic ethers such as dioxane as solvent for the reaction, the very good solvent power of the ethers or araliphatic compounds of the invention for sodium and potassium β-naphtholates is surprising so that the concentration of sodium and potassium β-naphtholates in the solvent may be very high. Since the araliphatic compounds and aromatic ethers of the invention have little or no volatility in steam, it is only water that is removed upon heating while the naphtholates remain in the solvent. By comparison therefore difficulties as regards recovery of the araliphatic compounds and waste water problems do not arise to any significant extent. Iron may be used as the material of construction without any increased formation of byproducts being observed. The operation of the plant is safe and simple, especially on an industrial scale. All these advantageous properties are surprising having regard to the prior art. It would have been expected that the araliphatic compounds which are of fairly high molecular weight or of bulky structure and aromatic ethers would have little or no solubility for carbon dioxide and/or the naphtholates and thus would have an inhibiting effect on the speed and yield of the reaction. Since naphthalene according to the statements in German Laid-Open Specification (DOS) No. 2,132,296 (at the bottom of page 8) gives poorer yields of end product than alkylnaphthalenes do, poorer results would have been expected in the case of araliphatic compounds having a plurality of aromatic nuclei and/or without terminal alkyl groups or in the case of aromatic ethers having a plurality of aromatic nuclei and/or a plurality of aralkoxy groups.

In the first stage of the reaction the starting mixture is heated continuously or intermittently to a temperature of at least 180° C, preferably from 200° to 280° C and particularly from 240° to 265° C at atmospheric or superatmospheric pressure. Generally, from 0.02 to 0.5 and preferably from 0.02 to 0.2 mole of potassium β-naphtholate is used per mole of sodium β-naphtholate and accordingly the amount of potassium and sodium hydroxide used for the production of the starting materials are conveniently molar ratios of potassium hydroxide to sodium hydroxide of from 0.02 : 1 to 0.5 : 1 and preferably from 0.02 : 1 to 0.2 : 1.

Araliphatic compounds or aromatic ethers are used in the preferred embodiments. These substances serve as reaction media, wholly or partly dissolve the naphtholates and are solvents or suspension agents for the reaction mixture. It is advantageous to use as the reaction medium an aralkyl compound which contains two, three or four benzene and/or naphthalene nuclei which are not fused with one another; the nuclei are preferably connected together by way of cyclohexylene groups, cyclopentylene groups and/or alkylene groups of one to eight and particularly one to four carbon atoms. In the case of cycloaliphatic members connecting two nuclei together it is advantageous for one nucleus to be fused with the cycloaliphatic radical but for the other nucleus not to be fused.

When two aromatic radicals are connected together by a cycloaliphatic radical, for example cyclohexylene or cyclopentylene, it may bear an aliphatic radical, for example alkyl, as a substituent, one of the aromatic radicals being connected direct to one carbon atom of the cycloaliphatic radical or fused with the cycloaliphatic radical and the other aromatic radical being connected direct to a carbon atom of an alkyl substituent. Preferred compounds are those of the formula:

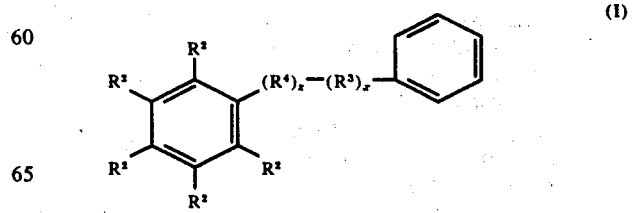

(I)

and particularly those of the formulae:

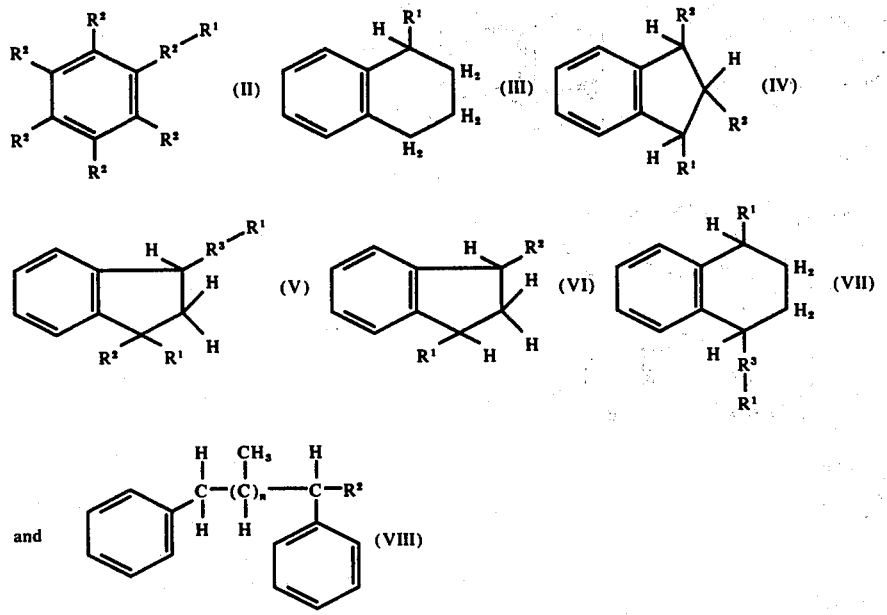

in which
R¹ is aryl, particularly phenyl or naphthyl;
R² is alkyl advantageously of one to four carbon atoms or hydrogen;
R³ is alkylene of one to eight carbon atoms and particularly of one to three carbon atoms;
R⁴ is a cycloalkylene ring of five or six carbon atoms which may be substituted by one or two alkyl groups of one to four carbon atoms and/or a phenyl or naphthyl radical and which is connected to the adjacent benzene nucleus or fused therewith;
z is zero or 1
x is zero or 1;
z and x together are 1 or 2; and
n is zero, 1 or 2.

When R⁴ is a cycloalkene ring fused with the aromatic nucleus substituted by the radical R², an adjacent radical R² is a member of this ring. Alkyl and alkylene radicals may be linear or branched. The said radicals may be substituted by groups which are inert under the reaction conditions, for example alkyl of one to three carbon atoms.

Examples of suitable solvents or suspension agents are: diphenylmethane, 2',4',5'-trimethyldiphenylmethane, 2',4',2'',4''-tetramethyldiphenylmethane, 1,2-diphenylethane, 1,1-diphenylethane, 1,4-diphenylbutane, naphthyltetrahydronaphthalene, phenyltetrahydronaphthalene, 1-phenyl-4-phenylbutyltetrahydronaphthalene, 1-phenyl-4-naphthylethyltetrahydronaphthalene, 1-phenyl-2,3-dimethylindan, 1,3-diphenylbutane, 1-phenylethyl-3-phenyl-3-methylindan, 1,4-diphenylbutane, 1-phenyl-2-methyl-3-phenylhexane; and compounds of the formula:

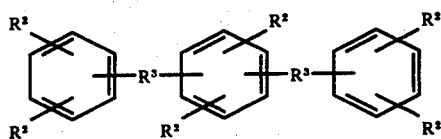

(IX), in which R² and R³ have the above meanings, for example the substances prepared by the process described in German Pat. No. 1,085,877 such as dibenzylbenzene, o-xylylxylene, m-xylylxylene, p-xylylxylene and the corresponding mixtures of isomers.

Dimers and oligomers of styrene, particularly 1-methyl-3-phenylindan and 1-phenyl-4-phenylethyltetrahydronaphthalene are especially preferred. These are secondary products of styrene some of which can be isolated from the bottoms of styrene distillation and some can be isolated by distillation in the dimerization of styrene into 1-methyl-3-phenylindan. The distillation bottoms may be used direct for the reaction according to the invention, conveniently after hydrogenation of the olefins such as 1,3-diphenylbutene, 1,3-triphenylhexene and methylstilbene contained therein. Other arylalkylbenzenes may be prepared by oligomerization of styrene. 1-methyl-3-phenylindan and 1-phenyl-4-phenylethyltetrahydronaphthalene in pure form and in the form of the said technical mixtures dissolve surprisingly large amounts of sodium and potassium β-naphtholates. The solvent power for sodium and potassium β-naphtholates is up to 80% by weight of sodium and potassium β-naphtholates at 250° to 260° C.

Advantageous aromatic ethers contain one, two, three or four unfused benzene and/or naphthalene nuclei with which each may have one, two or three aralkyl, cycloalkyl and/or alkyl radicals, preferably alkyl radicals, attached thereto by way of an oxygen atom, so that at least one of the said radicals is attached by way of an oxygen atom with one of the said nuclei and which moreover may be connected to one another by way of alkylene or a radical —O—R⁵—O— in which R⁵ is alkylene or aralkylene. Preferred aromatic ethers are those of the formula:

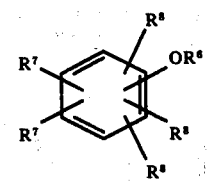

(X)

and particularly those of the formulae:

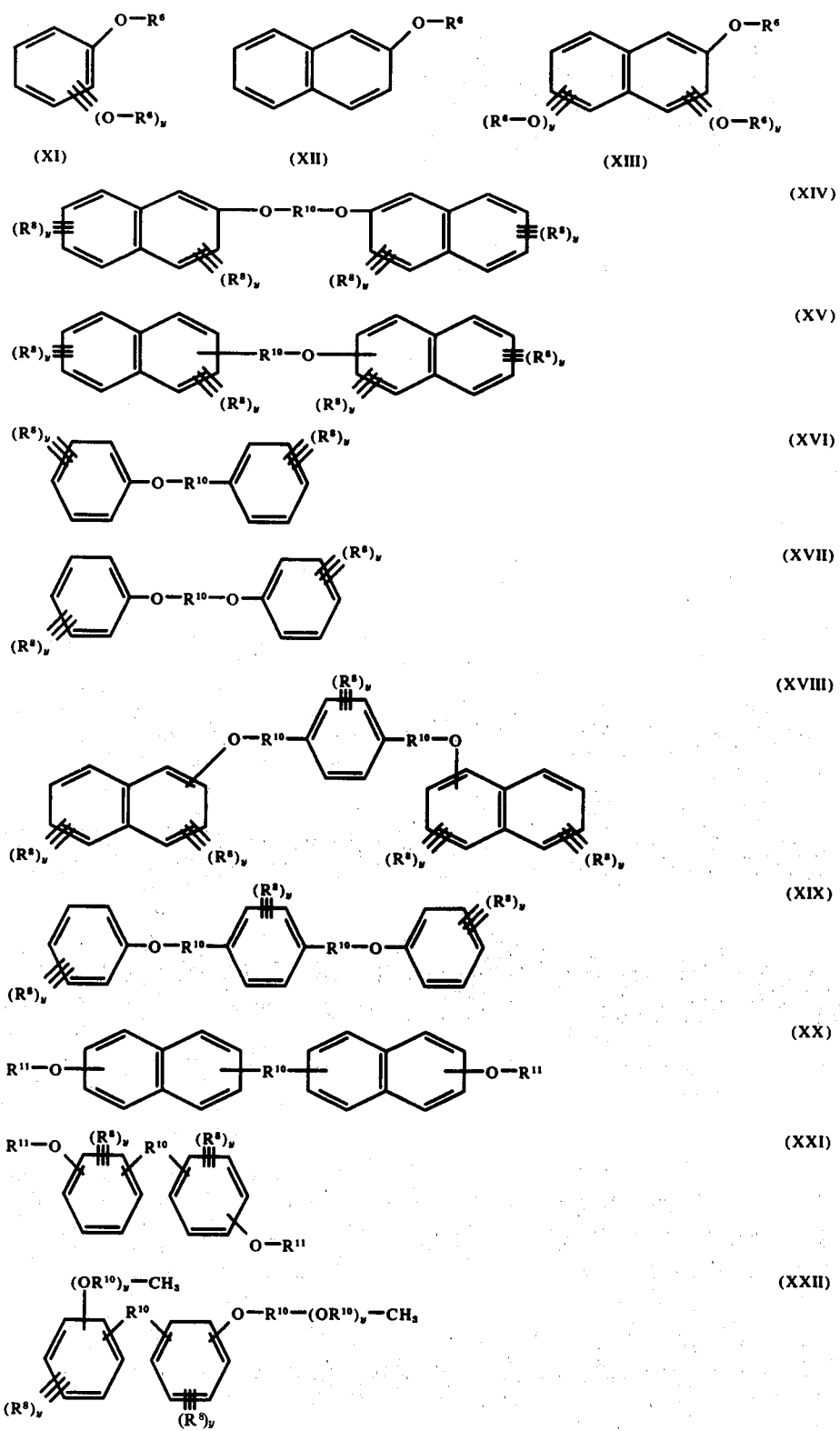
in which $R^6$ is alkyl of one to four carbon atoms, cyclopentyl or cyclohexyl, $-R^{10}-(OR^{10})_y-CH_3$,
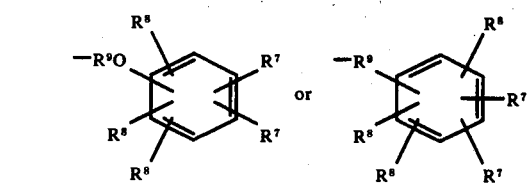
individiual radicals $R^7$ and $R^8$ may be identical or different and each is alkyl or alkoxy in each case of one to four carbon atoms, cycloalkyl or cycloalkoxy of five or six carbon atoms, hydrogen or $-(OR^{10})_y-CH_3$, moreover one $R^7$ may also be

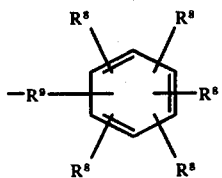

and two radicals $R^7$ may together be a nucleus fused with the benzene nucleus on the side a

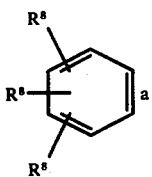

or the fused nucleus

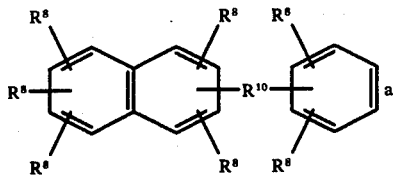

in which $R^8$ has the above meanings, $R^9$ is alkylene of two to four carbon atoms or the radical:

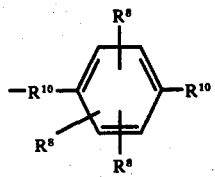

in which $R^8$ has the above meanings, $R^{10}$ is alkylene of two to four carbon atoms, $R^{11}$ is alkyl of one to four carbon atoms and y is zero, 1, 2 or 3.

The said alkyl and alkylene radicals may be linear or branched. The said radicals may also be substituted by groups which are inert under the reaction conditions, for example alkoxy or alkyl in each case of one to three carbon atoms.

Examples of suitable solvents or suspension agents are: resorcinol dimethyl ether, α-naphthol methyl ether, β-naphthol methyl ether, β-naphthol ethyl ether, β-naphthol propyl ether, ethylene glycol diphenyl ether, 1,2-dinaphthoxybutane, 1,2-dinaphthoxyethane, 1,3-diphenoxypropane, 1,4-diphenoxybutane, 1,5-diphenoxypentane, 1,2-diphenoxypropane, 1,3-diphenoxybutane, phenoxy-(γ-phenylpropyl) ether, (2'-methoxy)-phenylethyl phenyl ether, naphthyl-(2)-propyl phenyl ether, 1,3-di-(2'-methyl)-phenoxypropane, 1,4-di-(3'-methyl)phenoxybutane, 1,2-di-(2'-methyl)-phenoxyethane, 1,2-di-(3'-methyl)phenoxyethane, 1,2-di-(4'-methyl)-phenoxyethane, 1,2-di-(2'-methyl)phenoxypropane, 1,2-di-(3'-methyl)-phenoxypropane, 1,2-di-(4'-methyl)-phenoxypropane, ω,ω'-diphenoxy-1,4-diethylenebenzene, 2,4,5,8-tetramethoxynaphthalene, 4,5,8-triethyl-β-naphthol methyl ether, 4-cyclohexylphenyl methyl ether, β-naphthaol cyclohexyl ether, α-naphthol-(monobutoxy)-triethylene glycol ether, ω,ω'-dinaphthoxy-(2',2")-1,4-diethylenebenzene, 1,4-bis-(5'-methoxynaphthyl)-butane, 4,4'-dimethoxy-2,2'-dimethyldiphenylethane, and 1,3-diphenylpropane-4',4"-bis-(ω, ω'-ethoxydiethylene glycol) ether.

The easily accessible ethers of β-naphthol are particularly preferred, especially β-naphthol methyl ether and the reaction products of alkali metal naphtholates, alkali metal phenolates and alkali metal cresylates, for example sodium naphtholates, sodium phenolates and sodium cresylates with ω-dihalogen compounds, particularly with the easily accessible 1,2-dichloroethane, 1,2-dichloropropane and 1,4-dibromobutane. The aromatic ethers both in pure form and in the form of technical mixtures dissolve surprisingly large amounts of sodium and potassium β-naphtholates.

The reaction may be carried out with one or more than one araliphatic compound and/or one or more than one aromatic ether as the reaction medium. As a rule the araliphatic compounds or aromatic ethers used have a boiling point of at least 200° C and advantageously of from 270° to 400° C, preferably from 270° to 350° C and they are used in an amount of from 20 to 100% and preferably from 25 to 30% by weight based on naphtholate.

The naphtholates may be used as pure substances but it is convenient to combine the first stage of the process of the invention with the production of the naphtholate so that a three-stage process is carried out in a single vessel, preferably with all stages in the presence of the araliphatic compound or aromatic ether. The naphtholates may be prepared by one of the conventional production methods for naphthol using a sodium compound or potassium compound such as sodium carbonate, potassium carbonate, potassium hydroxide or sodium hydroxide for formation of the salt (Ullmanns Encyklopadie der technischen Chemie, volume 12, pages 603 and 604). The two naphtholates may be prepared separately from each other by the above methods and the reaction mixtures combined but it is more convenient to prepare the naphtholate mixture in a common reaction, for example, from β-naphthol, sodium hydroxide and potassium hydroxide and preferably in the preferred molar ratio of potassium hydroxide to sodium hydroxide of from 0.02 : 1 to 0.5 : 1 and particularly from 0.02 : 1 to 0.2 : 1.

The above molar ratio of total potassium hydroxide to total sodium hydroxide and of the alkali metal naphtholates is conveniently maintained in all the said embodiments.

The solution or suspension of β-naphtholates obtained in this way is optionally heated and used direct for the carboxylation reaction. The araliphatic compound may be used in the said ratio to the naphtholates.

Production of the naphtholates may be carried out at atmospheric or superatmospheric pressure, continuously or batchwise.

The mixture from naphthol production supplied to the first stage of the reaction according to the invention advantageously contains a total amount of sodium and potassium (calculated as sodium hydroxide and potassium hydroxide) which is a stoichiometric amount based on the total naphthol in the mixture. An excess above the stoichiometric amount, for example of up to 10% by weight, of naphthol based on the total amount of alkali (calculated as alkali metal hydroxide) may be present in the starting mixture if desired. It is also possible to heat to the reaction temperature β-naphthol, araliphatic compound or aromatic ether and aqueous caustic alkali solution, in the presence or absence of an inert gas such as nitrogen. When the starting mixture is heated, for example for from 30 to 60 minutes, water distils off.

In the second stage of the reaction (carboxylation) the mixture is carboxylated continuously or batchwise at a temperature of at least 180° C, preferably at from 200° to 280° C and particularly at from 240° to 265° C at atmospheric or superatmospheric pressure. The carboxylation is conveniently carried out at superatmospheric pressure, preferably at a pressure of from 2 to 50 atmospheres and particularly from 3 to 20 atmospheres and with an amount of carbon dioxide of from 0.5 to 10 moles and preferably from 0.5 to 2 moles based on naphtholate. The reaction period of the carboxylation is conveniently from one hour to five hours. The end product is isolated by a conventional method. For example the mixture may be cooled and the suspension of the salt of 2-hydroxy-3-naphthoic acid poured into water or, when an araliphatic compound or aromatic ether is used which has a boiling point similar to that of β-naphthol, the araliphatic compound or aromatic ether may be distilled off with the whole of the β-naphthol at subatmospheric pressure and the residue washed with water at from about 90° to 100° C. When for example there is used a trimer of styrene or of 1,4-diphenoxybutane the β-naphthol formed may also be distilled off after the end of the carboxylation reaction at subatmospheric pressure and the suspension of the salts of 2-hydroxynaphthalene-3-carboxylic acid stirred with water or poured into water.

The β-naphthol may also be extracted from the reaction mixture with the stream of carbon dioxide which is conveniently recycled; this is known as stripping. For example carbon dioxide is passed into the melt until the absorption of carbon dioxide subsides. Then the β-naphthol liberated is distilled off by applying a vacuum and the melt which remains is again carboxylated. These operations are repeated until no further carbon dioxide is absorbed and no further β-naphthol distils off; this is usually the case after from two to four carboxylations alternating with two or three distillations of the β-naphthol formed.

Acid is then added to the aqueous mixture to obtain the free carboxylic acid; it is possible to use a wide range of acids and methods of converting a salt into the corresponding acid. The pH of the aqueous mixture which contains the salt of 2-hydroxynaphthalene-3-carboxylic acid together with a small amount of sodium β-naphtholate is conveniently adjusted to about 5 to 60° to 70° C with aqueous hydrochloric acid (for example from 5 to 35% by weight strength); the β-naphthol liberated is extracted by an araliphatic compound or an aromatic ether and then the organic phase is separated from the aqueous phase; the portion of β-napthol which is precipitated after acidification of the aqueous phase to pH about 5 may also for example be filtered through a filter press. The aqueous phase freed from β-naphthol by extraction or filtration is then conveniently acidified to pH 3 with aqueous hydrochloric acid (for example of 5 to 35% by weight strength) at 85° to 95° C, stirred for from 5 to 15 minutes, then cooled for example to 50° C and suction filtered. Slight contamination of the 2-hydroxynaphthalene-3-carboxylic acid with 2-hydroxynaphthalene-6-carboxylic acid may easily be removed by making use of the far better solubility of the latter in hot water. The isomers can be separated from the waste water by cooling.

The 2-hydroxynaphthalene-3-carboxylic acid which can be prepared by the process of the invention is a valuable starting material for the production of dyes and is a coupling component for coating surface dyes and chrome dyes and is also a developer for diazotized dyes. The above publication, especially Ullmanns standard work, volume 12, page 609, may be referred to for further details of use.

The following Examples illustrate the invention. The parts referred to in the following Examples are by weight.

EXAMPLE 1

A stirred autoclave is charged with 1260 parts of β-naphthol, 592 parts of aqueous caustic soda solution (50% by weight) and 40 parts of aqueous caustic potash solution (85% by weight). The mixture is mixed well under nitrogen until it has heated up to an internal temperature of 260° C and is kept for 30 minutes at this temperature. Dehydration is then practically complete. Carboxylation is carried out in an autoclave at a temperature of 260° C with dry carbon dioxide at a pressure of 7 atmospheres. The absorption of carbon dioxide is monitored by a gas meter. After absorption has ended β-naphthol is distilled off at 20 mm and then in the manner described above carbon dioxide is again forced in. The β-naphthol is again distilled off and carboxylation is carried out for a third time. Within a carboxylation period of three hours a total of 300 parts of carbon dioxide is absorbed. The autoclave is then cooled and the reaction mixture is stirred with a solution of 90 parts of sodium hydroxide in 5000 parts of water at 95° to 100° C. While stirring vigorously the aqueous phase is acidified to pH about 6 with hydrochloric acid. The β-naphthol thus deposited is cooled to 30° C and suction filtered; the clear aqueous filtrate is acidified with hydrochloric acid (35% by weight) at a temperature of from 85° to 90° C to a pH of 3 and stirred for another ten minutes. The crystals of 2-hydroxynapthalene-3-carboxylic acid formed are suction filtered and dried in vacuo at 70° C. 510 parts of end product (68% of theory based on the reacted β-naphthol) is obtained with a melting point of 215° to 219° C.

EXAMPLE 2

A stirred autoclave is charged with 1260 parts of β-naphthol, 608 parts of caustic soda solution (50% by weight) and 27 parts of caustic potash solution (85% by weight). In the manner described in Example 1 to the autoclave is heated while stirring to an internal temperature of 260° C and kept at this temperature for 10 minutes. The residual moisture is removed at 40 mm from the autoclave during five minutes. Dehydration is practically complete and water is collected as distillate. Carbon dioxide is then passed into the autoclave at an internal temperature of 260° C up to a pressure of 7 atmospheres. Carboxylation followed by working up are carried out as described in Example 1. Carboxylation is carried out a total of three times in alternation with distilling off the β-naphthol formed twice, so that 300 parts of carbon dioxide is absorbed in a total of five hours. After working up as described in Example 1 530 parts of 2-hydroxynaphthalene-3-carboxylic acid (71% of theory based on β-naphthol reacted) is obtained with a melting point of 215° to 219° C.

EXAMPLE 3

A stirred autoclave is charged with 1260 parts of β-naphthol, 608 parts of caustic soda solution (50% by weight) and 27 parts of caustic potash solution (85% by weight) and also 400 parts of 1,2-di-(3'-methyl)-phenoxyethane. The autoclave is heated to an internal temperature of 260° C while stirring as described in Example 1. Residual moisture is removed from the autoclave at 100 mm during 15 minutes. Dehydration is then practically complete. Carbon dioxide is then introduced into the autoclave at an internal temperature of 260° C up to a pressure of 7 atmospheres. After the absorption of carbon dioxide has ended β-naphthol is distilled off at 15 mm and then 7 atmospheres of carbon dioxide is again forced in during 30 minutes. The autoclave is then cooled and the reaction mixture is stirred with a solution of 90 parts of sodium hydroxide in 5000 parts of water at 95° to 100° C and the organic phase is separated. The aqueous phase is acidified to about pH 6 with hydrochloric acid with efficient stirring and the β-naphthol thus deposited is suction filtered after it has been cooled to 30° C. The clear aqueous filtrate is acidified with hydrochloric acid (35% by weight) at a temperature of 85° to 90° C to a pH of 3 and stirred for another 10 minutes. The crystals of 2-hydroxynaphthalene-3-carboxylic acid thus formed are suction filtered and dried in vacuo at 70° C. 544 parts of end product (72% of the theory based on the β-naphthol reacted) is obtained having a melting point of 215° to 219° C.

EXAMPLE 4

A stirred autoclave is charged with 1260 parts of β-naphthol, 624 parts of caustic soda solution (50% by weight), 14 parts of caustic potash solution (85% by weight) and 400 parts of 1-phenyl-4-phenylethyltetrahydronaphthalene. As described in Example 1 the autoclave is heated to an internal temperature of 260° C while stirring and during 10 minutes the residual moisture is removed from the autoclave at this temperature and 100 mm. Carbon dioxide is then introduced into the autoclave up to a pressure of 7 atmospheres at the internal temperature of 260° C. After absorption of carbon dioxide has ended the β-naphthol formed is distilled off at 15 mm pressure and then carbon dioxide is forced in again at 7 atmospheres for 30 minutes. The autoclave is cooled and the reaction mixture is stirred with a solution of 90 parts of sodium hydroxide in 5000 parts of water at 95° to 100° C. The mixture of organic and aqueous phases is acidified at a temperature of 75° C with vigorous stirring so that the liberated β-naphthol is absorbed by the solvent. The organic phase is separated from the aqueous phase. The clear aqueous phase is heated to 85° to 90° C, acidified with hydrochloric acid to a pH of about 3 and stirred for another 10 minutes. After having been cooled to 50° C the crystals of 2-hydroxynaphthalene-3-carboxylic acid which have formed are suction filtered and dried in vacuo at 70° C. 560 parts of end product (75% of theory based on the reacted β-naphthol) is obtained having a melting point of 214° to 217° C.

We claim:

1. A process for the production of 2-hydroxynaphthalene-3-carboxylic acid which comprises heating β-naphthol and an aqueous solution of potassium hydroxide and of sodium hydroxide in a molar ratio of said respective hydroxides in the range of 0.02:1 to 0.5:1 to produce a mixture of sodium β-naphtholate and potassium β-naphtholate containing 0.02 to 0.5 mol of potassium β-naphtholate per mol of sodium β-naphtholate, in a first stage to a temperature of at least 180° C. in the absence of a solvent, then reacting said heated mixture of said naphtholates in a second stage at a temperature of at least 180° C. with carbon dioxide to form a mixture of the sodium and potassium salts of 2-hydroxynaphthalene-3-carboxylic acid, and acidifying said salts to convert them into 2-hydroxynaphthalene-3-carboxylic acid.

2. A process as claimed in claim 1 wherein the reaction is carried out in the first and second stage at a temperature of from 200° to 280° C.

3. A process as claimed in claim 1 wherein said molar ratio of said respective hydroxides is in the range of 0.02–0.2:1 and said mixture contains 0.02 to 0.2 mol of potassium β-naphtholate per mol of sodium β-naphtholate.

4. A process as claimed in claim 1 wherein the reaction in the second stage is conducted with an amount of carbon dioxide in the range of from 0.5 mol to 10 mols per mol of the naphtholates at 2–50 atmospheres.

* * * * *